US006572582B1

(12) United States Patent
Wong et al.

(10) Patent No.: US 6,572,582 B1
(45) **Date of Patent: *Jun. 3, 2003**

(54) MIXING SYSTEM FOR AN ACTIVE AGENT DELIVERY DEVICE

(75) Inventors: Patrick S. L. Wong, Burlingame, CA (US); Stephen S. Hwang, Palo Alto, CA (US); Vincent J. Ferrari, Foster City, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,655

(22) Filed: Nov. 23, 1999

Related U.S. Application Data

(62) Division of application No. 08/950,424, filed on Oct. 15, 1997, now Pat. No. 6,024,721
(60) Provisional application No. 60/028,704, filed on Oct. 18, 1996.

(51) Int. Cl.[7] .............................................. A61M 37/00
(52) U.S. Cl. ............................ 604/85; 424/473; 604/78
(58) Field of Search ............................ 604/48, 57, 59, 604/60, 77–79, 82–85, 89; 424/473, 451, 438, 464

(56) References Cited

U.S. PATENT DOCUMENTS 1,661,400 A 3/1928 Yehle
2,436,505 A 2/1948 DuRall
2,867,536 A 1/1959 Mead et al.
3,409,224 A 11/1968 Harp et al.
3,610,483 A 10/1971 Visconti et al.
3,845,770 A 11/1974 Theeuwes et al.
3,995,631 A 12/1976 Higuchi et al.
4,034,756 A 7/1977 Higuchi et al.
4,111,202 A 9/1978 Theeuwes et al.
4,320,759 A 3/1982 Theeuwes et al.
4,327,725 A 5/1982 Cortese et al.
4,449,983 A 5/1984 Cortese et al.
4,581,013 A 4/1986 Allen
4,765,989 A 8/1988 Wong et al.
4,792,333 A 12/1988 Kidder
4,981,468 A 1/1991 Benefiel et al.
5,094,861 A 3/1992 D'Auguste et al.
5,123,915 A 6/1992 Miller et al.
5,222,940 A 6/1993 Wilk
5,223,259 A 6/1993 Lackney
5,487,750 A 1/1996 Burchett et al.
5,509,605 A 4/1996 Cripe
5,707,353 A 1/1998 Mazer et al.
5,718,681 A 2/1998 Manning
5,772,685 A 6/1998 Crowe et al.
5,780,058 A * 7/1998 Wong et al. ................ 424/438
5,910,321 A * 6/1999 Wong et al. ................ 424/464
5,985,324 A * 11/1999 Wong et al. ................ 424/438
6,024,721 A * 2/2000 Wong et al. ................ 424/438
6,096,003 A * 8/2000 Wong et al. .................. 604/78

FOREIGN PATENT DOCUMENTS

DE 1906964 2/1969
WO WO 97/03634 2/1997

OTHER PUBLICATIONS

Kikendall, M.D. et al., Digestive Disease and Sciences, vol. 28, No. 2 (Feb. 1983), "Pill–Induced Esophageal Injury".
Derwent Abstract, Wk. 9637, B07, 96–363246/37, DE 19503104–A1, Tomasek J., 95.02.01, 95DE–1003104.

* cited by examiner

*Primary Examiner*—Michael J. Hayes
*Assistant Examiner*—Kathy L. Assadii
(74) *Attorney, Agent, or Firm*—Andrea G. Reister; Covington & Burling

(57) ABSTRACT

The present invention is directed to a mixing system for an active agent delivery device. The device comprises an elongate tubular member having first and second ends and a mixing system. The mixing system enables the entire dose of active agent to be entrained in a liquid. In use, liquid is drawn into the first end of the device, the mixing system mixes the liquid and active agent within the device and the active agent entrained in the liquid is drawn out of the second end of the member and into the patient's mouth.

8 Claims, 2 Drawing Sheets

MIXING SYSTEM FOR AN ACTIVE AGENT DELIVERY DEVICE

This application is a division of application Ser. No. 08/950,424 filed Oct. 15, 1997 now U.S. Pat. No. 6,024,721, and claims the benefit of U.S. Provisional Application No. 60/028,704, filed Oct. 18, 1996.

FIELD OF THE INVENTION

The present invention is related to the oral delivery of a liquid dispersion of an active agent. More particularly, it is a mixing system for mixing a liquid with an active agent in a delivery device. Proper mixing of the active agent and a liquid allows for accurate delivery of the dose of active agent.

BACKGROUND OF THE INVENTION

Tablets, capsules, caplets and many other types of devices have been used for oral delivery of active agents. These forms are relatively easy to manufacture and convenient for use in the hospital or other institutional settings or at home. Many different types of active agents have been incorporated into such dosage forms—ranging from analgesics to antibiotics to hormones.

There are patients that, because of age or infirmity, have difficulty swallowing solid oral dosage forms. According to Kikendall et al., *Digestive Diseases and Sciences* 28:2 (1983), there were 221 cases documented between 1970–1982 of tablet and capsule induced esophageal injury. The most commonly implicated drugs were tetracycline (108 cases), emepronium bromide (36 cases), potassium chloride (16 cases) and ferrous salts (12 cases).

In view of the above, various approaches have been proposed whereby swallowing of a large solid system is avoided as is described in the following patents and applications which are all incorporated by reference herein.

U.S. Pat. No. 2,436,505 to DuRall describes a pill douser for administering medicines in liquid form or in pills or tablets. The device has a bowl at the top for containing the medicine and a tube that can be submerged in a liquid held in a drinking glass. The liquid is drawn upward for administering the liquid and any pill or tablet present in the bowl.

U.S. Pat. No. 2,867,536 to Mead et al. describes an improved drinking straw where a soluble flavoring material is contained within an annular space contained within an inner and an outer tube. The inner tube has a bore through which liquid can be drawn. During Use, the upper and lower caps are removed, the flavoring material is emptied into the liquid and the flavored liquid is drawn up through the inner tube and into the mouth.

U.S. Pat. No. 3,610,483 to Visconti describes a dispensing device for liquid medication that is formed in the shape of a straw. A predetermined dose of liquid medication is loaded into the straw which is then capped at both ends until the medication is dispensed when a patient removes the caps and sucks air into the device.

U.S. Pat. No. 4,581,013 to Allen is directed to a doser for orally administering a medication. A tube with a removable closure and a radially extending plate supports a solid medication and permits passage of a stream of liquid. The tube is fitted on top of a straw that is placed into a liquid.

U.S. Pat. No. 4,792,333 to Kidder describes a tamper proof package for containing and orally administering a solid substance. A tube has two portions that are separated by a supporting and confining means that supports and confines the solid substance but permits fluid flow. The ends of the tube are hermetically sealed.

U.S. Pat. No. 4,981,468 to Benefiel et al. is directed to a unit dosage form for delivering a therapeutic agent in free-flowing form. A slanted grid supports the dose between two ends of a tube.

PCT Patent Application No. PCT/US96/11812 describes an oral active agent delivery system comprising a hollow chamber that contains discrete units of active agent. A fluid passing retainer prevents release of the discrete units but permits fluid entry into the chamber. The retainer is transportable with the fluid entering the system.

A variety of other oral delivery systems have been described. These include a medicated pacifier (U.S. Pat. No. 5,123,915 to Miller et al.) and a lollipop type device for delivery of a solid medicament (U.S. Pat. No. 5,223,259 to Lackney). None of these devices or the devices described previously provide for the delivery of a solid medicament into the oral cavity as a bolus dose, where the entire dose is delivered as a result of complete mixing of the active agent with a fluid.

SUMMARY OF THE INVENTION

Accordingly the present invention is directed to mixing an active agent with a liquid within an active agent delivery device. The delivery device comprises a tubular member with a first end and a second end. The first end is suitable for placement in a liquid and the second end is suitable for placement in the mouth of a patient. The device further comprises a lumen that contains a therapeutically effective amount of an active agent in the form of discrete units. The mixing system comprises a mixing chamber and a turbulence providing member for improved mixing of the liquid and active agent in the device.

DESCRIPTION OF THE DRAWINGS

The figures are not drawn to scale, but are set forth to illustrate various embodiments of the invention. Like numbers refer to like structures.

DETAILED DESCRIPTION OF THE INVENTION

The present invention provides mixing systems for oral active agent delivery devices. The active agent is in the form of discrete units and is contained within the lumen of an active agent delivery device. The mixing systems enable the entire dose of active agent to be entrained in a liquid to accurately deliver a measured dose of active agent to a patient.

Definitions

The term "discrete units" means the active agent in solid or particulate form.

The term "oral dosage form" means that the active agent is placed in a discrete unit that is delivered orally and is capable of maintaining its physical configuration and chemical integrity while housed within the delivery device.

The term "therapeutically effective amount" means the amount of the active agent needed to effect the desired pharmacologic, often beneficial, result.

The term "fluid passing active agent retainer" means a valve, plug, grid, restriction or the like that allows for passage of fluid but does not allow for passage of other ingredients such as the active agent that is contained in the delivery device.

The dispensing devices of the invention find use where it is inconvenient or unsafe to use oral dosage forms such as capsules or tablets. The devices may be particularly useful in geriatric or pediatric patient populations but they may also be useful for those who have difficulty swallowing capsules or tablets. A single delivery device or several devices can be administered to a patient during a therapeutic program.

Figure 1:
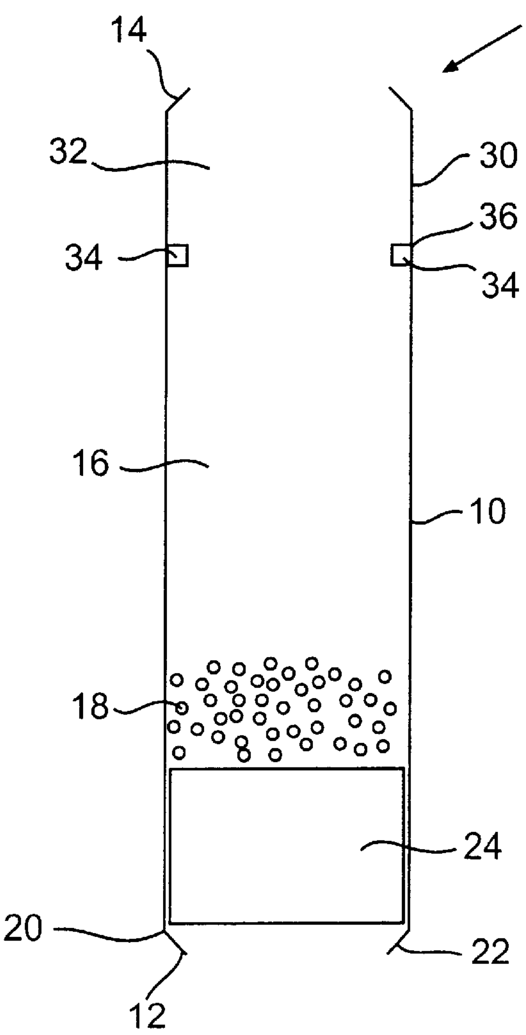
FIG. 1 is a side view of one embodiment of an active agent delivery device with a mixing system according to the invention.

FIG. 1 depicts, in a side view, one embodiment of the delivery device according to the invention. The device is in prepared form prior to placement in a fluid. Dispensing device 1 is shown in FIG. 1 to comprise an elongate tubular member 10 with a first end 12 and a second end 14. Contained within tubular member 10 is a lumen 16 that contains an active agent 18 and a fluid passing active agent retainer 20. The fluid passing active agent retainer 20 comprises a restriction 22 and plug 24. The restriction 22 is formed by crimping the end of tubular member 10. The inner diameter of the restriction 22 is smaller than the outside diameter of the plug 24 such that the active agent 18 and plug 24 are retained within the tubular member 10 but plug 24 can slide upwardly in lumen 16 as fluid is drawn therethrough.

Figure 2:
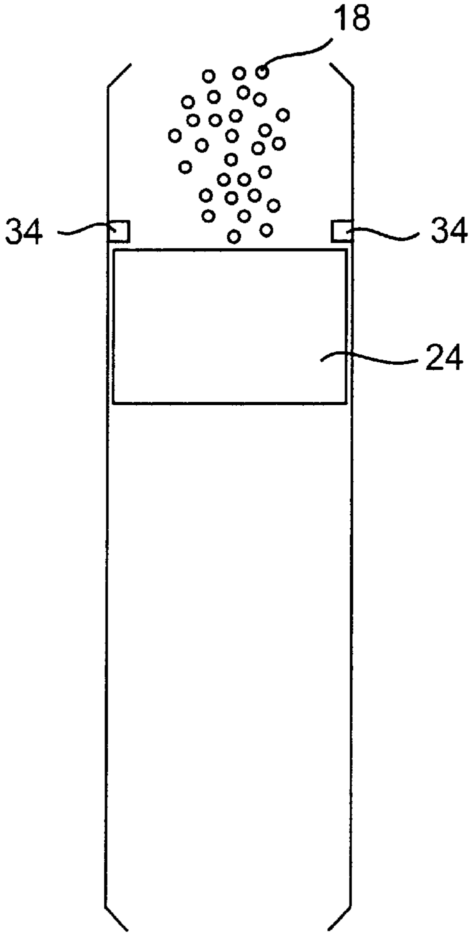
FIG. 2 is a side view of the device of FIG. 1 during active agent delivery.

FIG. 1 further shows a mixing system 30 for delivery device 1. The mixing system comprises a mixing chamber 32 and a turbulence providing member 34. The turbulence providing member 34 in the embodiment is a restriction in the lumen 16 and is shown as an annular ring attached to the inner surface 36 of the elongated tubular member 10. When in use, the first end 12 of the elongated tubular member 10 is placed in a fluid and the second end 14 is placed in the mouth of a patient. The patient begins to suck on the second end 14 of member 10 and fluid is drawn up into lumen 16 up through plug 24. The fluid, active agent 18, and plug 24 are then sucked up toward mixing chamber 32. The fluid and active agent 18 enter the mixing chamber 32 but the plug is stopped by the turbulence providing member 34. The discrete units of active agent 18 are entrained in the fluid and sucked out of the second end 14 of the elongated tubular member 10 and into the patient's mouth. FIG. 2 shows the device of FIG. 1 when the plug 24 is seated against the turbulence providing member 34 and the dose of active agent 18 is entrained in the turbulent liquid being delivered to the patient.

Figure 3:
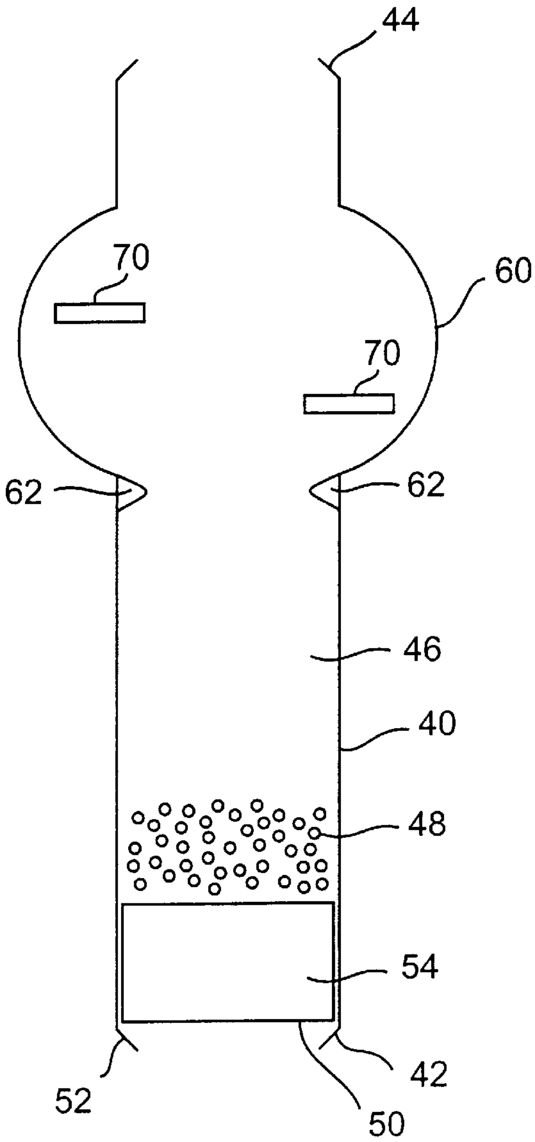
FIG. 3 is a side view of a second embodiment of an active agent delivery device with a mixing system according to the invention.
Figure 4:
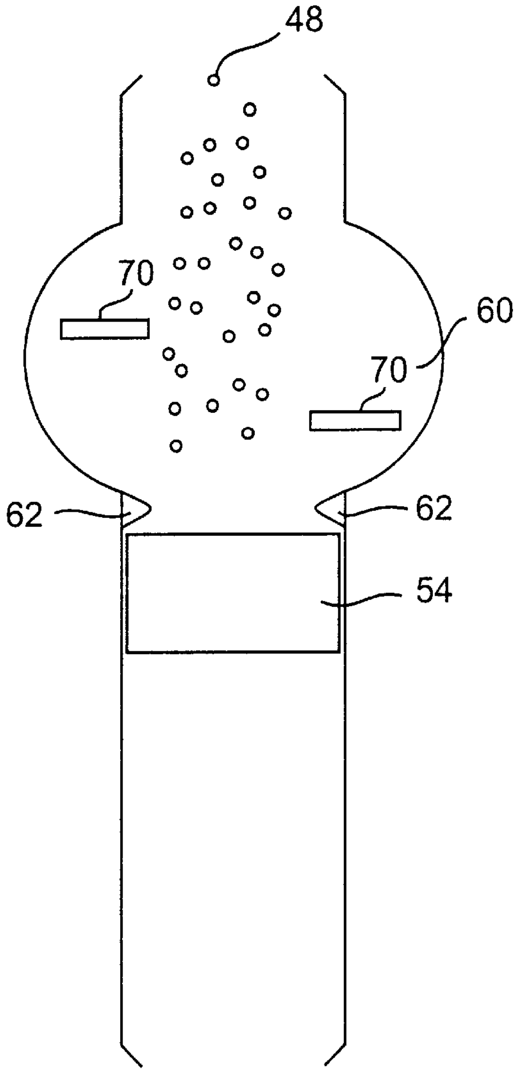
FIG. 4 is a side view of the system of FIG. 3 during active agent delivery.

FIG. 3 shows a second embodiment of the mixing system of the invention. As in the embodiment shown in FIG. 1, the device comprises an elongated tubular member 40 with a first end 42 and a second end 44. A lumen 46 contains an active agent 48 in the form of discrete units and a fluid passing active agent retainer 50. The fluid passing active agent retainer 50 comprises a restriction 52 and a plug 54. The mixing system comprises a mixing chamber 60 that is integral with the elongate tubular member 40 and detents 62 in the lumen 46. The mixing chamber 60 has an inner diameter that is larger than the maximum inner diameter of the remainder of the tubular member 40. The turbulence providing member in this embodiment are the detents 62 and the mixing chamber 60. When in use, the first end 42 of the elongated tubular member 40 is placed in a fluid and the second end 44 is placed in the mouth of a patient. The patient begins to suck on the second end 44 of the member 40 and fluid is drawn into the lumen 46 of tubular member 40 through plug 54. The fluid and active agent 48 are then sucked up into the mixing chamber 60, the plug 54 is held in place by detents 62. The fluid and active agent 48 are then sucked out of the second end 44 of the elongated tubular member 40 and into the patient's mouth. FIG. 4 shows the device of FIG. 3 when the plug 54 is positioned below the mixing chamber 60 and the dose of active agent 48 is being delivered to the patient.

The active agent itself may be in liquid, solid, or semisolid form and formulated into discrete units. The agents may be soluble and insoluble, charged or uncharged molecules, components of molecular complexes or nonirritating, pharmacologically acceptable salts and may contain additional materials such as binders, coating materials, or stabilizers such that the active agent is formed into one or more discrete units. The discrete units may be designed in a multitude of ways to provide a specific drug delivery profile. One embodiment comprises an active agent that is in particulate form. These particulates are generally between about 50 and 2000 μm in diameter, usually between about 100–500 μm in diameter. Where the particulate has an unpleasant taste, the particulate may be taste masked by methods that are well known in the art. The particulates may be designed to provide immediate delivery of the active agent, they may be coated to provide for prolonged release or delayed pulse release of the active agent, or they may be designed to provide for a combination of immediate, pulsed and/or prolonged delivery of active agent. The particulates may be coated with an enteric coating to provide for targeted release of the active agent.

In other embodiments, the active agent may be in liquid form and may be contained within a soft gelatin capsule or within a solid oral dosage form. These dosage forms may include, matrix or other types of tablets, pellets and elongated tablets where the height to diameter ratio exceeds one, capsules, microcapsules, elementary osmotic pumps, such as those described in U.S. Pat. No. 3,845,770, mini osmotic pumps such as those described in U.S. Pat. Nos. 3,995,631, 4,034,756, and 4,111,202, and multichamber osmotic systems referred to as push-pull and push-melt osmotic pumps, such as those described in U.S. Pat. Nos. 4,320,759, 4,327,725, 4,449,983, and 4,765,989 all of which are incorporated herein by reference.

The term "active agent" refers to an agent, drug, compound, composition of matter or mixture thereof which provides some pharmacologic, often beneficial, effect. This includes foods, food supplements, nutrients, drugs, vitamins, and other beneficial agents. As used herein, the terms further include any physiologically or pharmacologically active substance that produces a localized or systemic effect in a patient. The active drug that can be delivered includes antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of active agents useful in this invention include zafirlukast, prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-b-estradiol, ethinyl estradiol, ethinyl estradiol 3-methyl ether, prednisolone, 17-b-hydroxyprogesterone acetate, 19-nor-progesterone, norgestrel, norethindrone, norethisterone, norethiederone, progesterone, norgesterone, norethynodrel, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captopril, mandol, guanabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidinei sucralfate, etintidine, tertatolol, minoxidil, chlordiazepoxide, diazepam, amitriptyline, tetracycline, metronidazole, amoxicillin, clavulanate potassium, ganciclovir, acyclovir, zidovudine and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin and luteinizing hormone.

It is to be understood that more than one active agent may be delivered in a device of this invention, and that the use of the term "agent" in no way excludes the use of two or more such agents. Combination products such as those described, for example, in U.S. Pat. No. 5,256,684 for the treatment of ulcers (tetracycline, metronidazole and bismuth subsalicylate) and for the treatment of AIDS (zidovudine (AZT), a protease inhibitor and 3TC) are particularly suited for delivery using the present invention.

The amount of active agent employed in the delivery device will be that amount necessary to deliver a therapeutically effective amount of the agent to achieve the desired result. In practice, this will vary widely depending upon the particular agent, the severity of the condition, and the desired therapeutic effect. However, the device is generally useful for active agents that must be delivered in fairly large doses of from about 100 mg to 5000 mg, usually in the range of from about 250 mg to about 2500 mg. However, since the devices may also be useful in pediatric patients, doses in the ranges of 25 to 50 mg are also contemplated herein.

Representative materials for forming devices including the active agent formulation chamber, the elongated tubular member and the mixing chamber include, without limitation, paper, plastic such as propylene/styrene copolymers, polypropylene, high density polyethylene, low density polyethylene, ethylene vinyl acetate copolymer and the like. The devices usually have an outer diameter of between about 5 and 15 mm. The lumen has a diameter that is usually between about 4 and 14 mm and often between about 5 and 12 mm. The devices are between about 10 and 30 cm in length.

The fluid passing active agent retainer permits the free flow of fluid but prohibits passage of the active agent from the device prior to delivery. Where the retainer comprises a one-way plug or valve, the plug or valve will seal the straw at atmospheric pressure. When suction is applied, fluid will be drawn into the lumen of the device. Where the plug a density of less than one, it will ascend to the top as the active agent is delivered into the oral cavity. When suction is no longer applied, the plug will remain in the highest position it reached during sipping.

The mixing chamber in the present invention is shown as an integral portion of the elongated tubular member, but it may also be a second tubular member placed on top of the active agent containing tubular member. The mixing chamber may have the same inner diameter as the remainder of the elongated tubular member or it may have an inner diameter that is between about 10 and 100% larger than the maximum inner diameter of the elongated tubular member, preferably between about 20 and 60% larger.

The turbulence providing member in the present invention may be a restriction, detents or vanes in the lumen of the elongated tubular member, baffles 70 in the mixing chamber, the plug, or a combination of the above. This member functions to create turbulence such that there is good mixing of the active agent and the liquid.

The drinkable fluid that is used for suspending the active agent formulation by sipping through the active agent formulation chamber is preferably any good-tasting liquid including but not limited to water, juice, milk, soda, coffee, tea etc. Care must be taken to ensure compatibility of the fluid with the active agent formulation.

The above description has been given for ease of understanding only. No unnecessary limitations should be understood therefrom, as modifications will be obvious to those skilled in the art.

We claim:

1. An active agent delivery device, comprising:

a tubular member that defines a lumen, said tubular member having a first end suitable for placement in a liquid and a second end suitable for placement in the mouth of the patient;

an active agent in the form of discrete units disposed in said lumen;

a mixing chamber spaced apart from the first end of said tubular member;

a fluid passing active agent retainer, wherein said fluid passing active agent retainer prevents release of the active agent from the first end of said tubular member while permitting the liquid to enter said tubular member, said fluid passing active agent retainer being transportable toward said mixing chamber upon application of suction by the patient so that liquid and active agent are drawn into said mixing chamber; and means for providing turbulence, wherein said means for providing turbulence increases turbulence of the liquid drawn into said mixing chamber, wherein said means for providing turbulence is configured to prevent said fluid passing active agent retainer from being drawn into said mixing chamber.

2. The delivery device of claim 1, wherein said discrete units are selected from the group consisting of particulates, oral dosage forms and combinations thereof.

3. The delivery device of claim 1, wherein said discrete units provide for prolonged delivery of said active agent.

4. The delivery device of claim 1, wherein said discrete units provide for immediate delivery of said active agent.

5. The delivery device of claim 1, wherein said discrete units provide for delayed pulsed delivery of said active agent.

6. The delivery device of claim 1, wherein a therapeutically effective amount of active agent is disposed in said lumen.

7. The delivery device of claim 6, wherein the therapeutically effective amount is between 100 and 5000 mg.

8. The delivery device of claim 1, wherein said active agent is selected from the group consisting of antibiotics, antiviral agents, anepileptics, analgesics, anti-inflammatory agents, and bronchodilators.

* * * * *